United States Patent [19]
Huchler et al.

[11] 4,196,130
[45] Apr. 1, 1980

[54] MANUFACTURE OF CYCLIC ETHERS

[75] Inventors: Otto H. Huchler, Limburgerhof; Siegfried Winderl, Heidelberg-Wieblingen; Herbert Mueller; Herwig Hoffmann, both of Frankenthal, all of Fed. Rep. of Germany

[73] Assignee: BASF Aktiengesellschaft, Fed. Rep. of Germany

[21] Appl. No.: 931,851

[22] Filed: Aug. 7, 1978

Related U.S. Application Data

[63] Continuation of Ser. No. 786,405, Apr. 11, 1977, abandoned.

[51] Int. Cl.$^2$ ............................................ C07D 307/08
[52] U.S. Cl. ................................................. 260/346.11
[58] Field of Search ..................................... 260/346.11

[56] References Cited

U.S. PATENT DOCUMENTS 2,251,895  8/1941  Reppe et al. ............... 260/346.11

OTHER PUBLICATIONS

Gmelin, 8th Edition, Aluminum, Part B.
Ullmanns Encyklopädie der Technischen Chemie, 4th Edition, vol. 7, p. 294.

*Primary Examiner*—Richard Raymond
*Attorney, Agent, or Firm*—Keil & Witherspoon

[57] ABSTRACT

Cyclic ethers are manufactured by eliminating water from corresponding diols in the presence of aluminum oxide which has been obtained by precipitating aluminum hydroxide from an alkali metal aluminate solution by means of an acid and calcining the hydroxide at from 300° to 1,000° C.

3 Claims, No Drawings

MANUFACTURE OF CYCLIC ETHERS

This is a continuation of application Ser. No. 786,405 filed Apr. 11, 1977, now abandoned.

The present invention relates to a process for the manufacture of cyclic ethers by dehydrating $\alpha,\omega$-diols in the presence of aluminum oxide.

Numerous processes of this type, e.g. the dehydration of 1,4-butanediol to tetrahydrofuran (THF), have been disclosed. The prior art, up to 1955, is comprehensively covered in Liebigs Annalen der Chemie, 596 (1955), 81.

Dehydrating agents cited are phosphoric acid, sulfuric acid, oxalic acid, coppers sulfate, magnesium chloride, zinc chloride and many others. Using these acidic compounds, the elimination of water is conventionally carried out in the liquid phase at up to 250° C.

If temperatures above 250° C. are used, certain other catalysts, e.g. oxides of aluminum, titanium, zirconium and tungsten, as well as bleaching earths and phosphates, also become active. Since butanediol, in particular, boils at 245° C., the conversion of this compound is either carried out in the gas phase or under superatmospheric pressure (cf. German Pat. No. 711,709). However, if the reaction temperature is very high, a significant amount of butadiene is formed.

The conventional processes, however, suffer from a number of disadvantages. Thus, if soluble catalysts are used, there is a significant consumption of catalyst and the yield in general does not exceed 90%. Improved processes disclosed later, e.g. in German Pat. No. 850,750, where the reaction is carried out by means of a cation exchanger based on a synthetic resin, provide no essential improvement in respect of the above disadvantages, particularly since the life of commercial exchanger resins at reaction temperatures above 150° C. is low.

The use of small amounts of concentrated sulfuric acid, as disclosed in German Pat. No. 1,043,342, requires that the synthesis be carried out in apparatus having a corrosion-resistant lining, and is therefore relatively expensive. In addition, experience has shown that in this process hardly more than 10,000 parts of butanediol are converted per part by weight of sulfuric acid; after this, the catalyst is spent, due to impurities, and must be destroyed. In view of the fact that, for example, tetrahydrofuran is a large-scale industrial product, the amount of catalyst to be destroyed is a substantial disadvantage.

German Pat. No. 700,036 purposes using aluminum oxide as the catalyst for the manufacture of tetrahydrofurans from butylene glycols. According to the working instructions of Example 5 of the said patent, this method gives a yield of 92.5% of tetrahydrofuran from 1,4-butylene glycol if 10 percent by weight of active aluminum oxide is used as the catalyst and the reaction is carried out at from 185° to 200° C.

Repeating the process of the above patent has shown that the use of aluminum oxide, even of the "active" aluminum oxide referred to but not defined in more detail, does not necessarily give good results.

It is an object of the present invention to provide a process, and a catalyst based on aluminum oxide, by means of which the conversion of diols to at least 5-membered cyclic ethers can be carried out in a trouble-free manner, with high yield and little catalyst consumption, and which in particular can also be carried out with the conventional industrial grades of diols, which are not particularly pure.

We have found that this object is achieved, according to the invention, by carrying out the elimination of water in the liquid phase and using an aluminum oxide which is suspended in the reaction mixture and has been obtained by precipitating aluminum hydroxide from an aqueous alkali metal aluminate solution by means of an acid and then heating the hydroxide at from 300° to 1,000° C., preferably from 400° to 800° C. This is surprising since it has been disclosed that regardless of the initial modification of the aluminum orthohydroxide or meta-hydroxide, $\gamma$-aluminum oxide is always formed.

The manufacture of aluminum oxide by the above method, which as a rule leads to $\gamma$-aluminum oxide, has already been disclosed and is not a subject of the present invention. It is described, for example in Gmelin, 8th edition, Aluminum, Part B, and Ullmanns Encyklopädie der Technischen Chemie, 4th edition, volume 7, page 294.

We have found that particularly active catalysts are obtained if steps are taken to ensure that during the precipitation process the pH does not fall below 6, even in limited zones of the reaction mixture. Hence, it is necessary to ensure vigorous mixing if the precipitation is carried out with a mineral acid. Mixing is less critical if precipitation is carried out with carbon dioxide. The activity of the catalyst is also effected by the washing process after precipitation. The aluminum hydroxide should be as free from alkali metal as possible.

A particularly active and therefore preferred aluminum oxide has a pH, measured by means of a glass electrode, of from 5 to 8, advantageously of from 5.5 to 7.5, in a stirred aqueous slurry. This pH can, furthermore, where necessary, be readily set up by adding small amounts of organic or inorganic acids of low volatility, e.g. oxalic acid, glutaric acid, succinic acid, maleic acid, fumaric acid, propionic acid, benzoic acid, phthalic acid, phosphoric acid and sulfuric acid, or of bases, e.g. oxides, hydroxides or carbonates of alkali metals or alkaline earth metals, or, where appropriate, amines of low volatility, e.g. tributylamine or tridecylamine.

Some cyclic ethers obtainable by the process may be represented by the formula

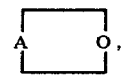

werein A is alkylene of 4 to 8 carbon atoms.

The process is also applicable to the manufacture of those cyclic ethers where alkylene contains oxygen in the chain; for example, 1,4-dioxane is a cyclic ether which can be manufactured advantageously by the process of the invention from diethylene glycol.

The process is particularly valuable for the manufacture of olefinically unsaturated cyclic ethers, e.g. of 2,5-dihydrofuran, which may be obtained by dehydrating (cis)-but-2-ene-1,4-diol. Generally speaking, the residue A mentioned above consists of an optionally olefinically unsaturated bivalent hydrocarbon chain, which may be substituted by 1 or 2 oxygen (ether) atoms in the chain.

It is true that the manufacture of dihydrofuran in the gas phase over an aluminum oxide catalyst has been disclosed, but this process gives up to 30% of by-products, some of which are difficult to remove, e.g. crotonaldehyde, hydroxyisobutyraldehyde, 2,3-dihydrofuran, furan and tetrahydrofuran (cf. German Pat. No. 695,219).

In contrast, the process of German Pat. No. 1,211,219, in which dihydrofuran is obtained in the liquid phase over an aluminum oxide catalyst, appears advantageous, in that it gives a yield of more than 95%. However, we have found, on repeating this process, that the catalysts described in the said patent very rapidly lose their selectivity. The longer the catalysts are used, the more by-products are formed. In particular, an increasing proportion of furan is formed. In addition, the reaction product becomes increasingly yellow. As soon as 100 parts of butenediol have been converted per part of catalyst, the yield falls from, for example, an initial value of 95% to about 80%. The color number of the distillate is from about 200 to 300 APHA units.

It is here that the present invention provides a remedy in that it recognizes the reasons why the prior proposals are unreliable or not feasible on an industrial scale, or shows that the special surface structure of a specific aluminum oxide is a decisive factor in the performance of the oxide as a dehydration catalyst. The universal applicability of the catalyst of the invention to virtually all relevant cyclizing reactions deserves special comment.

The new process gives virtually quantitative yields, provides as high a catalyst productivity as desired, and does not pollute the environment. Since the reaction mixture does not contain any corrosive substances, production equipment made from inexpensive constructional materials, e.g. conventional apparatus steel, may be used.

The process offers a particular advantage if undistilled crude butanediol, which may be contaminated by sodium formate or calcium formate, is used (see, for example, German Laid-Open Application DOS No. 2,303,619). Using the process according to the invention, the formates can be removed from the catalyst by washing with water or dilute acid.

High reaction speeds are attainable with the new process. They depend on the chosen reaction temperature and the amount of catalyst. At 210° C., in continuous operation, from 1 to 3 parts of tetrahydrofuran can be manufactured from butanediol per part by weight of catalyst per hour. The dehydration in accordance with the new process is carried out at from 160° to 230° C., preferably from 175° to 215° C. In general, the reaction is carried out under conventional pressures, i.e. at atmospheric pressure or slightly above or slightly below. When working under reduced pressure it is merely necessary to ensure that the boiling point of the butanediol should not be below the reaction temperature. The amount of catalyst used evidently does not depend on the chemical details, but on technological circmstances, and depends, for example, on the achievable rate of distillation, the reactor geometry and the like. In general, the catalyst is used in the form of a suspension of from 1 to 30 percent strength by volume, the particle size of the catalyst being from 0.001 to 5 mm.

In order, for example, to stabilize the reaction temperature, the dehydration can also be carried out in the presence of a chemically inert diluent. Examples of suitable diluents are hydrocarbons, e.g. gasoline fractions, high-boiling ketones or ethers, e.g. dodecane, decanone or dihexyl ether. In general, the use of a diluent can be dispensed with.

Whilst the process can be carried out batchwise, it is advantageous to employ continuous operation; in that case, a particularly advantageous method is to introduce the diol to be converted into the reaction mixture, whilst stirring, at the rate at which the cyclic ether is taken off at the top of the reaction vessel via an appropriate fractionating column. Since there are no side-reactions, the material obtained at the top of the column as a rule consists of the pure product together with the water formed and with any water which may have been introduced together with the starting material.

EXAMPLE 1

The process is carried out in a glass flask equipped with a stirrer and a fractionation attachment. The catalyst used is a mixture of 95% of boehmite and 5% of bayerite, which has been obtained by precipitating sodium aluminate with nitric acid and has, before use, been dried at from 120° to 200° C. and been heated for 12 hours at 400° C. The aluminum oxide has a particle size of from 40 to 250 $\mu$m; 1 part, as a slurry in 2 parts of water, has a pH of 7. Using this catalyst slurry, 940 parts of 1,4-butanediol are converted to tetrahydrofuran per hour, in quantitative yield.

COMPARATIVE EXPERIMENT

If the catalyst is not heated to 400° C. and is only dried, only 450 parts of butanediol are converted per hour.

COMPARATIVE EXPERIMENT

The procedure and apparatus described in Example 1 are used. The catalyst employed is the same amount of an aluminum hydroxide (boehmite) which has been obtained by precipitating aluminum sulfate with sodium hydroxide solution and has been dried at from 120° to 200° C. The particle size of the catalyst is from 40 to 250 $\mu$m. Before use, the catalyst is heated at 400° C. for 12 hours. In this case, 480 parts of butanediol can be converted per hour.

If the catalyst is dried at from 120° to 200° C. but is not heated at 400° C., and is then brought to a pH of 6.8, in an aqueous slurry, by treatment with phosphoric acid, 200 parts of 1,4-butanediol are converted to tetrahydrofuran per hour.

EXAMPLES 2 to 5

The apparatus, reaction conditions and catalyst described in Example 1 are used, and various $\alpha,\omega$-diols are dehydrated. The Table which follows shows the results achieved.

| | Diol | Reaction temperature (°C.) | Parts of converted diol/hour | Yield of cyclic ether (% of theory) |
|---|---|---|---|---|
| 2. | 1,5-Pentanediol | 210 | 252 | 99 (pentamethylene oxide) |
| 3. | 3-Methyl-1,5-pentanediol | 200 | 480 | 100 (4-methyltetrahydropyran) |
| 4. | 1,6-Hexanediol | 250 | 230 | 96 (hexamethylene oxide) |
| 5. | 2,5-Hexanediol | 198 | 607 | 100 2,5-dimethyltetrahydrofuran) |

We claim:
1. In a process for the manufacture of tetrahydrofuran by dehydrating 1,4-butanediol in the liquid phase in the presence of aluminum oxide which is suspended in the reaction mixture the improvement which comprises: using aluminum oxide in the process which has been obtained by precipitating aluminum hydroxide from an aqueous alkali metal aluminate solution by mixing a mineral acid with the alkali metal aluminate solution, at a pH above 6 and thereafter heating the hydroxide at a temperature of from about 400° to 800° C.

2. A process as set forth in claim 1, wherein the aluminum oxide in aqueous suspension or slurry has a pH of from 5 to 8, as measured by means of a glass electrode.

3. A process as set forth in claim 2, wherein the aluminum oxide has a pH of from 5.5 to 7.5.

* * * * *